Feb. 8, 1955 E. S. BOERNER Plant Pat. 1,347
ROSE PLANT
Filed May 3, 1954
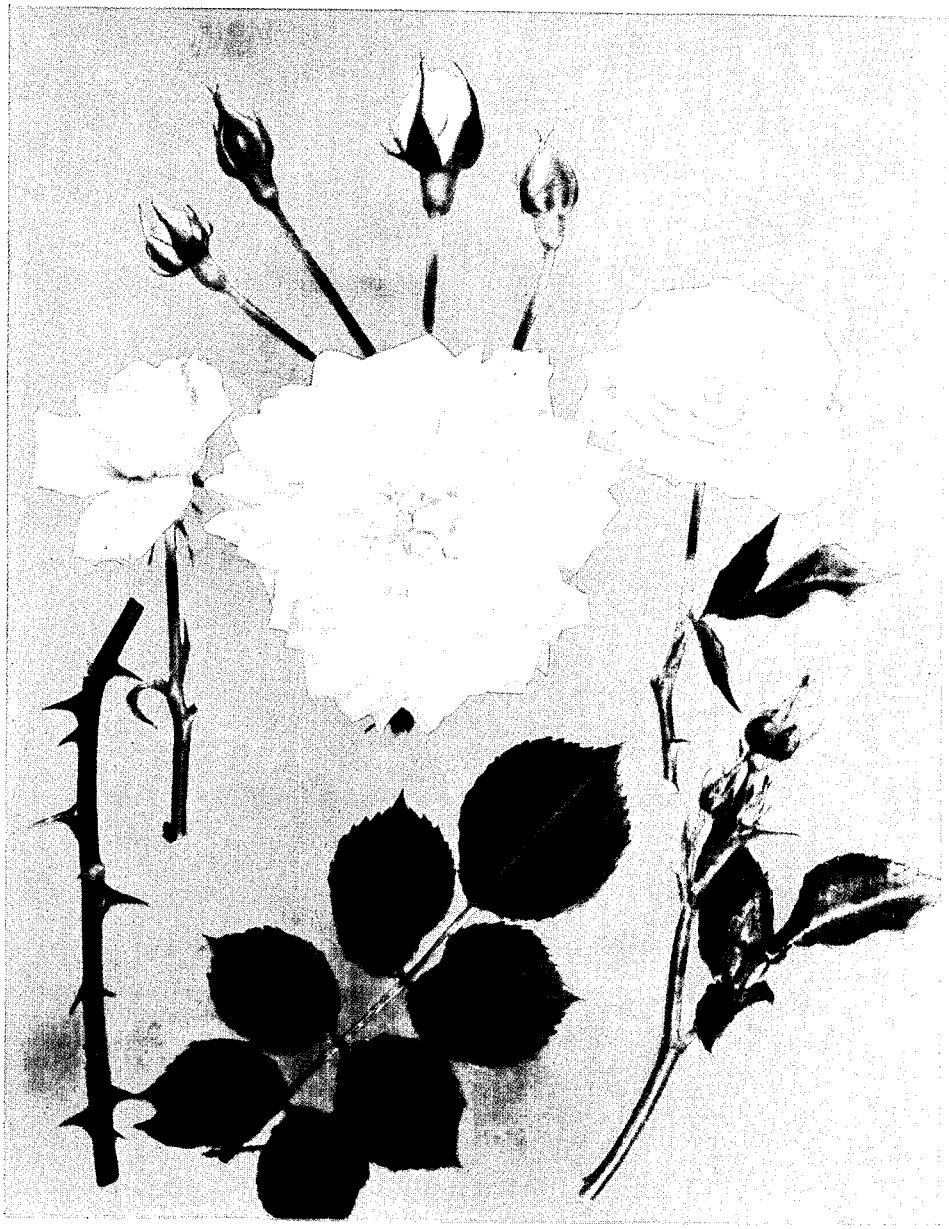
Inventor
E. S. Boerner
By: Robb & Robb
Attorneys.

United States Patent Office

Plant Pat. 1,347

Patented Feb. 8, 1955

1,347

ROSE PLANT

Eugene S. Boerner, Newark, N. Y., assignor to Jackson & Perkins Company, Newark, N. Y., a corporation of New York Application May 3, 1954, Serial No. 427,402

1 Claim. (Cl. 47—61)

The present invention relates to a new and distinct variety of rose plant of the large-flowered polyantha class, which was originated by me by crossing an unnamed and unpatented seedling of "Pinocchio" (Plant Patent No. 484) with the variety "Pigmy Gold" (Plant Patent No. 1,114).

The primary objective in making this cross was to produce a more healthy, bushy White Floribunda rose variety of the "Pinocchio" type. This objective was fully achieved, as evidenced by the fact that my new variety is particularly characterized as to novelty by the compact and bushy form of the plant, its White flowers of "Pinocchio" form and which are lightly overcast with Sea-Foam Yellow, its medium size foliage which is overcast with Claret Brown when young and which in the mature stage becomes Empire Green, and its free production of flower clusters.

These characteristics and distinctions represent a unique and desirable combination in a rose variety of this class, and distinguish my new variety from its parents, as well as from all other varieties of its class.

Asexual reproduction of my new variety by budding at Newark, New York, and also at Pleasanton, California, shows that the foregoing characteristics and distinctions come true to form and are established and transmitted through succeeding propagations.

The accompanying drawing shows typical specimens of the flowers, foliage and stems of my new variety in different stages of development, and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
- *Seed parent.*—An unnamed seedling of "Pinocchio."
- *Pollen parent.*—"Pigmy Gold."

Classification:
- *Botanic.*—Larger-flowered polyantha.
- *Commercial.*—Floribunda.

FLOWER (Observations made from specimens grown in a greenhouse at Newark, New York in the latter part of the month of March, and in the early afternoon.)

Blooming habit: Recurrent—continuous.

Bud:
- *Size.*—Medium.
- *Form.*—Ovoid; is not affected by wet or hot weather.
- *Color.*—When sepals first divide—Light Dull Green-Yellow, Plate 17. When petals begin to unfurl—Pale Dull Green-Yellow, Plate 17. When half blown: inside of petals—White, Plate 53, lightly overcast with Cartridge Buff, Plate 30; reverse of petals—White, Plate 53, lightly overcast with Ivory Yellow, Plate 30.
- *Sepals.*—Branched; curl back when petals begin to unfurl. Color: inside—Glass Green, Plate 31; outside—Light Elm Green, Plate 17.
- *Calyx.*—Color—Light Elm Green, Plate 17. Shape—pear. Size—small. Aspect—smooth. Odor when rubbed—none.
- *Peduncle.*—Length — medium. Aspect — smooth.
- *Strength.* — erect; slender. Color — Biscay Green, Plate 17.
- *Opening.*—Opens up well; is not affected by adverse weather conditions.

Bloom:
- *Size.*—Medium; average size when fully expanded—2½ inches.
- *Borne.*—Several together and in rounded clusters.
- *Stems.*—Medium length; normal strength.
- *Form (when first open).*—Fully open. Permanence—retains its form to the end, but outer petals curl back.
- *Petalage.*—Very double; from 75 to 80 petals under normal conditions.
- *Color.*—Center of flower—White, Plate 53, lightly overcast with Sea-Foam Yellow, Plate 31. Outer petals—White, Plate 53. Base of petals (aiglet)—Sea-Foam Yellow, Plate 31. Inside of petals—White, Plate 53. Reverse of petals—White, Plate 53. General tonality from a distance—White, Plate 53.
- *Discoloration.*—General tonality at end of first day—White, Plate 53, lightly overcast with Marguerite Yellow, Plate 30. Second day—White, Plate 53. Third day—White, Plate 53.

Petals:
- *Texture.*—Thin; is not affected by wet or hot weather.
- *Appearance.*—Inside—satiny. Outside—shiny.
- *Form.*—Notched.
- *Arrangement.*—Imbricated (regularly arranged shingle-like).
- *Petaloids in center.*—Few; small.
- *Persistence.*—Drop off cleanly.
- *Fragrance.*—Moderate. Nature—tea (average hybrid tea scent).
- *Lasting quality.*—On the plant—long. As cut flowers—long.

GENITAL ORGANS

Stamens, anthers: Small; few; regular around styles. Color—Pale Green Yellow, Plate 5.

Stamens, filaments (threads): Short. Color—Pale Viridine Yellow, Plate 5.

Pollen: Color—Straw Yellow, Plate 16.

Styles: Columnar; uneven length; medium length; thin.

Stigmas: Color—Marguerite Yellow, Plate 30.

Ovaries: All enclosed in calyx.

Hips: None.

Seeds: None.

PLANT

Form: Bush.

Growth: Vigorous; bushy; compact.

Foliage: 5 to 7 leaflets.
- *Size.*—Medium.
- *Quantity.*—Abundant.
- *Color.*—New foliage: upper side—Oil Green, Plate 5, lightly overcast with Claret Brown, Plate 1; under side—Lettuce Green, Plate 5, lightly overcast with Claret Brown, Plate 1. Old foliage: upper side—Empire Green, Plate 32; under side—Light Elm Green, Plate 17.
- *Shape.*—Oval pointed.
- *Texture.*—Upper side — smooth. Under side—smooth.
- *Ribs and veins.*—Ordinary.
- *Edge.*—Serrated (saw-toothed).
- *Serration.*—Single; small.
- *Leaf stem.*—Color—Light Hellebore Green, Plate 17. Under side—Prickles.
- *Stipules.*—Short; bearded.

Wood:
- *New wood.*—Color—Calla Green, Plate 31. Bark—smooth.
- *Old wood.*—Color—Cress Green, Plate 31. Bark—smooth.

Thorns:
- *Thorns.*—Quantity: on main stalks from base—ordinary; on laterals from stalk—ordinary. Form—narrow base; medium length; some straight and some hooked downward. Color (when young)—Old Rose, Plate 13. Position—irregular.
- *Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by its compact and bushy plant, its White flowers of "Pinocchio" form, lightly overcast with Sea-Foam Yellow, the medium size of its foliage which is overcast with Claret Brown color when young, but which changes in color to Empire Green in the mature stage, and its free production of flower clusters.

No references cited.